US009585619B2

(12) United States Patent
Benzel et al.

(10) Patent No.: US 9,585,619 B2
(45) Date of Patent: Mar. 7, 2017

(54) REGISTRATION OF HEAD IMPACT DETECTION ASSEMBLY

(75) Inventors: Edward C. Benzel, Gates Mills, OH (US); Vincent J. Miele, Bridgeport, WV (US); Adam J. Bartsch, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 596 days.

(21) Appl. No.: 13/399,949

(22) Filed: Feb. 17, 2012

(65) Prior Publication Data

US 2012/0220893 A1 Aug. 30, 2012

Related U.S. Application Data

(60) Provisional application No. 61/444,281, filed on Feb. 18, 2011.

(51) Int. Cl.
*A61B 5/00* (2006.01)
*A42B 3/04* (2006.01)
(Continued)

(52) U.S. Cl.
CPC .............. *A61B 5/682* (2013.01); *A42B 3/046* (2013.01); *A61B 5/067* (2013.01); *A61B 5/1121* (2013.01);
(Continued)

(58) Field of Classification Search
CPC ....... A42B 3/046; A61B 5/067; A61B 5/1121; A61B 5/682; A61B 5/1126; A61B 5/7267; A61B 2503/10
(Continued)

(56) References Cited

U.S. PATENT DOCUMENTS

| 5,539,935 A | 7/1996 | Rush, III |
| 5,621,922 A | 4/1997 | Rush, III |

(Continued)

FOREIGN PATENT DOCUMENTS

| JP | 06174740 A | 6/1994 |
| JP | 2002141841 A | 5/2002 |

(Continued)

OTHER PUBLICATIONS

Whitman E. McConnel et al., "Human Head and Neck Kinematics After Low Velocity Rear-End Impacts—Understanding whiplash", Paper 952724, Society of Automotive Engineers, 1995, pp. 215-238.*

(Continued)

*Primary Examiner* — Alexander Satanovsky
(74) *Attorney, Agent, or Firm* — Tarolli, Sundhiem, Covell & Tummino LLP

(57) ABSTRACT

Systems and methods are provided for registering a sensor assembly, implemented on a base apparatus, to a desired location associated with a head of a user. A position of a reference point on the base apparatus is determined relative to an external anatomical landmark of the user. A position of the external anatomical landmark is determined relative to the desired location. The position and orientation of the sensor assembly is determined relative to the desired location according to the determined position and orientation of the sensor assembly relative to the reference point, the determined position of the reference point relative to the external anatomical landmark, and the position of the external anatomical landmark relative to the desired location.

1 Claim, 6 Drawing Sheets

(51) Int. Cl.
*A61B 5/06* (2006.01)
*A61B 5/11* (2006.01)

(52) U.S. Cl.
CPC .......... *A61B 5/1126* (2013.01); *A61B 5/7267* (2013.01); *A61B 2503/10* (2013.01)

(58) Field of Classification Search
USPC ............ 702/41, 42, 141; 345/440, 473, 619; 600/553
See application file for complete search history.

(56) References Cited

U.S. PATENT DOCUMENTS

| | | | |
|---|---|---|---|
| 5,676,673 | A | 10/1997 | Ferre et al. |
| 5,978,972 | A | 11/1999 | Stewart et al. |
| 6,491,699 | B1 | 12/2002 | Henderson et al. |
| 6,508,747 | B1 | 1/2003 | Cook |
| 6,879,932 | B2 * | 4/2005 | Baudou et al. ............... 702/150 |
| 6,925,851 | B2 | 8/2005 | Reinbold et al. |
| 6,941,952 | B1 | 9/2005 | Rush, III |
| 7,384,380 | B2 | 6/2008 | Reinbold et al. |
| 2003/0217582 | A1 | 11/2003 | Reinbold et al. |
| 2005/0177335 | A1 | 8/2005 | Crisco, III et al. |
| 2005/0177929 | A1 * | 8/2005 | Greenwald et al. ............... 2/425 |
| 2006/0047447 | A1 | 3/2006 | Brady et al. |
| 2006/0074338 | A1 | 4/2006 | Greenwald et al. |
| 2006/0189852 | A1 | 8/2006 | Greenwald et al. |
| 2007/0287596 | A1 | 12/2007 | Case, Jr. et al. |
| 2008/0208073 | A1 | 8/2008 | Causevic |
| 2008/0269579 | A1 | 10/2008 | Schiebler |
| 2008/0306707 | A1 | 12/2008 | Vock et al. |
| 2008/0306996 | A1 | 12/2008 | McClellan et al. |
| 2009/0000377 | A1 | 1/2009 | Shipps et al. |
| 2009/0088619 | A1 * | 4/2009 | Turner et al. .................. 600/383 |
| 2011/0181419 | A1 * | 7/2011 | Mack et al. ............... 340/573.1 |
| 2012/0046536 | A1 * | 2/2012 | Cheung et al. ............... 600/407 |

FOREIGN PATENT DOCUMENTS

| | | |
|---|---|---|
| KR | 2002-0045720 | 6/2002 |
| KR | 2003-0093735 | 12/2003 |
| WO | WO-99/10052 A1 | 3/1999 |
| WO | WO 02/25635 A2 | 3/2002 |
| WO | WO-02/066118 A1 | 8/2002 |
| WO | 03063119 A2 | 7/2003 |
| WO | 03063119 A3 | 7/2003 |
| WO | WO-03/063119 A2 | 7/2003 |
| WO | WO-2005/077115 A2 | 8/2005 |
| WO | 2010051844 A1 | 5/2010 |

OTHER PUBLICATIONS

Harry G. Armstong et al. "Anthropometry. and Mass Distribution for Human Analogues. vol. I: Military Male Aviators", Final Report, Yellow Springs, Ohio, Mar. 1988, 53 pages.*

Chou et al., "On the Kinematics of the Head Using Linear Acceleration Measurements", *J. Biomechanics*, 9:607-613 (1976).

Crisco et al., "An Algorithm for Estimating Acceleration Magnitude and Impact Location Using Multiple Nonorthogonal Single-Axis Accelerometers", *Journal of Biomechanical Engineering*, 126:849-854 (2004).

Rowson et al., "Six Degree of Freedom Head Acceleration Measurements in Football Players", *Injury Biomechanics Research*, Proceedings of the 35th International Workshop, 85-92 (undated) (Abstract).

Pages i through 45 of the MSc Thesis of Sarah J. Manoogian, submitted to the faculty of the Virginia Polytechnic Institute and State University entitled "Analysis of Linear Head Accelerations from Collegiate Football Impacts" (2005).

Miele et al., "Objectifying When to Halt a Boxing Match: A Video Analysis of Fatalities", *Neurosurgery*, 60:307-316 (2007).

Olvey et al., "The Development of a Method to Measure Head Acceleration and Motion in High-Impact Crashes", *Neurosurgery*, 54:672-677 (2004).

Takhounts et al., "Analysis of 3D Rigid Body Motion Using the Nine Accelerometer Array and the Randomly Distributed In-Plane Accelerometer Systems" Website: www-nrd.nhtsa.dot.gov/pdf/esv/esv21/09-0402.pdf, undated, pp. 1-10.

Viano et al., "Concussion in Professional Football: Comparison with Boxing Head Impacts—Part 10", *Neurosurgery*, 57:1154-1172 (2005).

The International Search Report and Written Opinion, mailing date Mar. 26, 2012, pp. 1-10.

Hu, Sc.D., Anthony, Validation of an Instrumentation . . . , 1977 Workshop, Physical Science Lab., NM State Univ., Las Cruces, NM 88003. pp. 1-35.

Nusholtz, Guy S., et al., Reference Frames and Direct Head Impacts, 1977 Workshop, pp. 1-12.

Extended European Search Report for 11807594.4, mailed Jan. 23, 2015, pp. 1-6.

Extended European Search Report for 11807595.1, mailed Jan. 28, 2015, pp. 1-5.

Extended European Search Report for Application No. 11807596.9, mailed Feb. 5, 2015, pp. 1-6.

* cited by examiner

REGISTRATION OF HEAD IMPACT DETECTION ASSEMBLY

RELATED APPLICATIONS

This application claims priority to U.S. Provisional Patent Ser. No. 61/444,281, filed Feb. 18, 2011, the subject matter of which is hereby incorporated by reference.

FIELD OF THE INVENTION

The present invention relates to systems and methodologies for diagnosis of medical conditions, and, in particular, is directed to systems and methods for detecting and characterizing head impacts.

BACKGROUND OF THE INVENTION

There are over forty-seven million athletes under the age of twenty-four who participate in contact sports like football, basketball, hockey, soccer, boxing, and mixed martial arts (MMA) each year in the United States. Each of these young athletes is at risk for concussive traumatic brain injury (cTBI) and long-term brain dysfunction due to repeated head impact. These young athletes, with developing neurological systems, sustain a large portion of the 3.8 million cTBI occurring yearly and are at heightened risk of developing deleterious long-term neurological, physiological, and cognitive deficits. The head impact conditions responsible for cTBI and potential long-term deficits in athletes are unknown.

SUMMARY OF THE INVENTION

In accordance with an aspect of the present invention, a method is provided for registering a sensor assembly, implemented on a base apparatus, to a desired location associated with a head of a user. A position of a reference point on the base apparatus is determined relative to an external anatomical landmark of the user. A position of the external anatomical landmark is determined relative to the desired location. The position and orientation of the sensor assembly is determined relative to the desired location according to the determined position and orientation of the sensor assembly relative to the reference point, the determined position of the reference point relative to the external anatomical landmark, and the position of the external anatomical landmark relative to the desired location.

In accordance with another aspect of the present invention, an impact monitoring system is provided for determining an acceleration associated with an impact to a head of a human being. A mouthpiece assembly includes a plurality of sensors configured to measure at least one of a linear acceleration at a mouth of the human being, an angular acceleration at the mouth, an angular velocity at the mouth, and an orientation of the head during the impact to the head. A processing component includes a sensor interface configured to receive a measured position of an external anatomical landmark on the head relative to a reference point on the mouthpiece assembly and at least one anthropometric parameter of the head. The sensor interface determines an acceleration of a desired point within the head from the measured position, the at least one anthropometric parameter, and the at least one of a linear acceleration, an angular acceleration, an angular velocity and an orientation of the head at the associated measurement point during the impact to the head. A post-processing component is configured to communicate the determined acceleration at the desired point within the head to an observer via an associated output device.

In accordance with yet another aspect of the present invention, a method is provided for registering a sensor assembly, implemented on a mouthpiece apparatus, to a center of gravity of a head of a user. The mouthpiece apparatus is positioned within a mouth of the user. A position and an orientation of each of a plurality of sensors positioned within the mouthpiece apparatus are determined with respect to a known landmark, such as a tab, nub or extension, on an anterior portion of the mouthpiece apparatus. A position of the landmark is determined relative to a tragion of the user. The location of the tragion relative to the center of gravity is estimated from one or both of a known relationship and anthropometric parameters. The location and orientation of each sensor is determined relative to the center of according to the determined position and orientation of the sensor relative to the apparatus landmark, the determined position of the apparatus landmark relative to the tragion, and the position of the tragion relative to the center of gravity.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6 illustrates one example of a method for classifying an impact into an event class;

DETAILED DESCRIPTION OF THE INVENTION

In accordance with an aspect of the present invention, systems and methods for accurate registration of one or more sensor assemblies to determine accelerations at a desired location on a mammalian head are provided. To this end, sensor assemblies can be fixedly attached to the head in one or more locations, and the measurements taken at each location can be used to calculate kinematics and kinetics taking place at the desired location, including a center of gravity of the head. From this data, it is possible to accurately estimate the effects of a given impact on a user, allowing an observer to act to protect a user in response to an impact, or sequence of impacts, ranging in severity from minor to severe.

To allow for accurate measurement of the impact at a desired location, such as a center of gravity of the head, the position sensor assembly can be determined, relative to the desired location, via a registration process. To maximize the accuracy of this determination, particularly when the registration process is performed by a coach, parent, or other non-professional, a daisy chain registration process is proposed. In this process, the position of a landmark on the device relative to an anatomical landmark is determined. The anatomical landmark is selected such that it is easily identifiable, it is accessible for measurement, and such that the position of the landmark is precisely known, or at least better known that the position of the sensor apparatus, relative to the desired location. Once the relative position of the sensor and the landmark is ascertained, the known relationship and/or various anthropometric parameters can be used to determine a relative position of the sensor assembly and the desired location. In some implementations, for example, when the desired location is the center of gravity, this relative position can be represented as a time-varying function, allowing for a more accurate determination of the acceleration.

Figure 1:
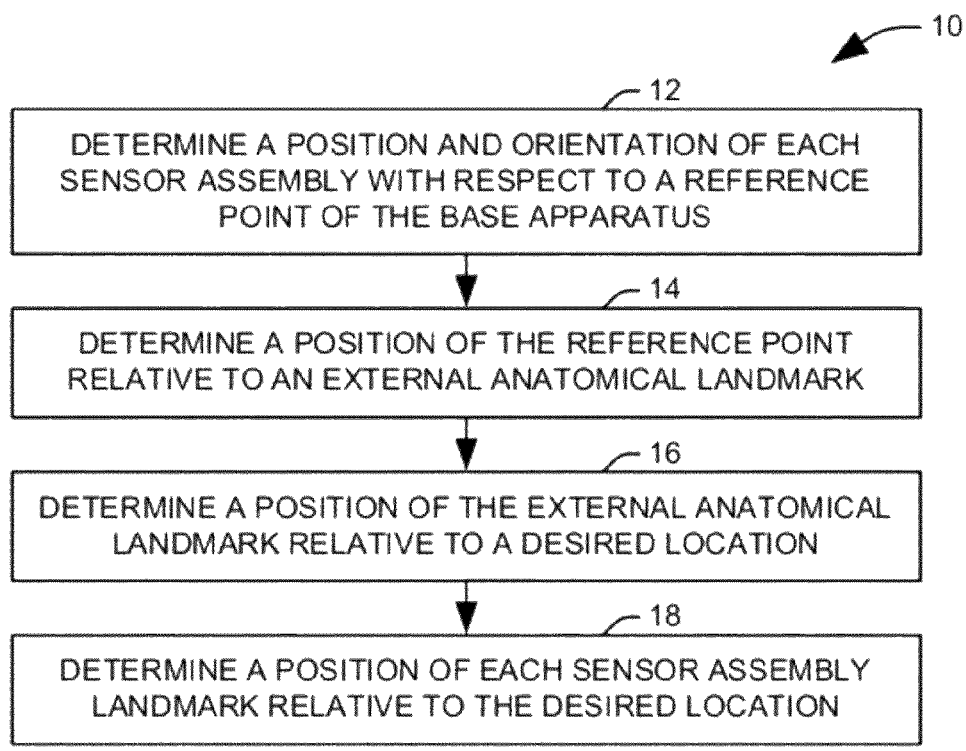
FIG. 1 illustrates a method for registering a sensor assembly, implemented on a base apparatus, to a desired location associated with a head of a user in accordance with an aspect of the present invention.

FIG. 1 illustrates a method 10 for registering a sensor assembly, implemented on a base apparatus, to a desired location associated with a head of a user in accordance with an aspect of the present invention. At 12, a position and orientation of each sensor assembly is determined with respect to a reference point on the base apparatus. For example, a reference frame associated with the base apparatus can be established with the reference point near its origin, such that the coordinates of each sensor in that reference frame substantially represent the position of the sensor relative to the reference point. It will be appreciated that the sensors can be located at the substantially the same position, and that position can be used as the origin, such that this step is unnecessary. In one implementation, the base apparatus is a mouthpiece, and the reference point is a landmark, such as a tab, nub or ridge, on an anterior portion of the mouthpiece. In this implementation, one or more angular velocity sensors can be located at the origin, with one of more of linear accelerometers positioned posterior and superior of the origin in the wings of the mouthpiece.

At 14, a position of the reference point on the base apparatus is determined relative to an external anatomical landmark of the user. For example, with the base apparatus fixed to the head of the user, a secondary reference frame associated with the immediate region around the base apparatus can be established. An orientation of the reference frame associated with the base apparatus can be established relative to the secondary reference frame, and an origin of the secondary reference frame can be established from one or more anatomical landmarks associated with the region. The reference point on the base assembly can be located within the secondary reference frame to allow the coordinates of the various sensors to be easily translated into the secondary reference frame. In the mouthpiece implementation, the secondary reference frame is established in and around the mouth, and the local anatomical landmarks can include any of the central incisors, the lateral incisors, the canines, the first premolars, the second premolars, the first molars, the second molars, the third molars, the alare, the subnasale, the labiale superius, the left and right labiale superius, the chelion, the stomion, the labiale inferius, the sublabiale, the pogonion, and the menton of the user.

Once the secondary reference frame is established, an orientation of the secondary reference frame relative to a head surface reference frame can be determined. An origin of a head surface reference frame can then be determined from the external anatomical landmark. In one implementation, the external anatomical landmark is utilized as the origin of the head surface reference frame. The precise location of the external anatomical landmark relative to the secondary reference frame or the reference point on the base apparatus can be determined via any of a number of methods. For example, one or more anthropometric parameters can be measured and used to determine the relative location of a head or facial feature having a known location in the secondary reference frame and the external anatomical landmark. For example, one of more of a head breadth, a head depth, a head length, an auditory length, and a head circumference can be used to determine the relative positions of the two features. Other methods can include determining the relative position via photogrammetry or via computerized mapping of the head surface via a set of digitized points.

At 16, the location of the external anatomical landmark is determined relative to the desired location. This can include determining a relative orientation between the head surface reference frame and a reference frame associated with the desired location, although they will often coincide. This can be accomplished, for example, using a computerized mapping, as described above, to locate or estimate the location of the desired location, or estimating the relative location from known relationships between the two locations and/or one or more anthropometric parameters. For example, it has been determined that the center of gravity of the average human head is generally about seven-tenths of a centimeter superior and about two and six-tenths centimeters anterior to the tragion or external auditory meatus. In an implementation in which the center of gravity is the desired location and the tragion is the external landmark, the relative location of the two points can be estimated according to this known relationship. In practice, this estimate can be adjusted according to measured anthropometric parameters, such that either or both the distance and direction of this average relative position can be adjusted for specific individuals.

At 18, the location and orientation of the sensor assembly relative to the desired location is determined. For example, the location of each sensor assembly relative to the desired location can be determined as a series of coordinate transforms, given the known relationships in the origins and orientations of the reference frame associated with the base apparatus, the secondary reference frame, the head surface reference frame, and the desired location. This daisy-chain registration process provides an accurate representation of the positions of arbitrarily placed sensors, allowing for flexibility in sensor deployment. In general, firm attachment of a sensor assembly to the head is painful and not tolerable for more than a few minutes at a time. Unfortunately, a secure mounting is necessary in order to rectify measurement error. By facilitating the use of a mouthpiece apparatus in sensor placement, daisy-chain registration allows the sensors to be placed in a fixed relationship with the head that is completely repeatable. Unlike other mounting locations, sweat, hair length, padding compression, and similar factors do not affect the sensor placement.

Figure 2:
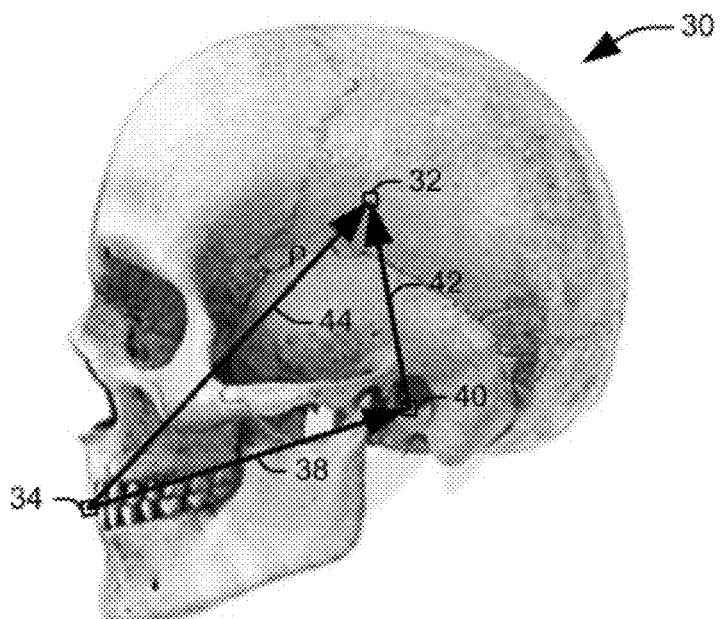
FIG. 2 illustrates one example of a determination of the relative location of the desired location and the sensor assembly for an exemplary implementation.

FIG. 2 illustrates one example 30 of the determination of the relative location of the desired location and the sensor assembly for an implementation in which the desired location is the center of gravity 32 and the sensor assembly is located just anterior to an external protrusion 34, such as a tab, nub or extension, on a mouthpiece serving as the base apparatus. The external protrusion 34 can be implemented as to be easily removable at the end of the registration process. A first vector 38 representing the relative location of the external protrusion 34 to the tragion 40 can be determined, for example, via photogrammetry, computerized mapping of the head surface via a set of digitized points, or the determination of one or more anthropometric parameters. A second vector 42, representing the relative location of the external protrusion 34 to the tragion 40, can be determined, for example, via photogrammetry, computerized mapping of the head surface via a set of digitized points, or the determination of one or more anthropometric parameters. A third vector 44, which serves as the base vector, p, representing the relative location of the external protrusion 34 to the center of gravity 32, can be determined by transforming the first and second vectors 38 and 42 into a common coordinate system and determining their sum.

Figure 3:
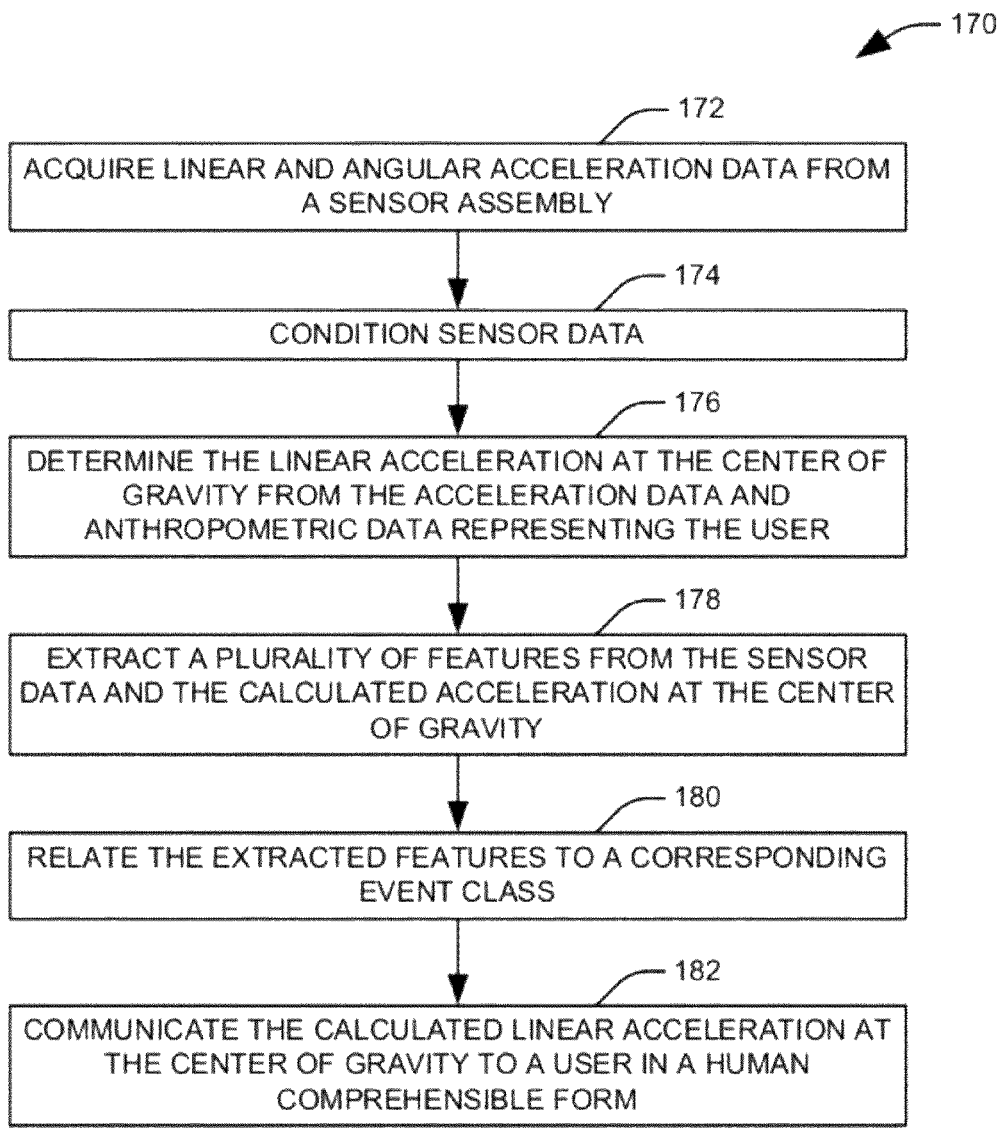
FIG. 3 illustrates an impact monitoring system configured to detect and characterize impacts to a mammalian head.

FIG. 3 illustrates one example of an impact monitoring system 50 configured to detect and characterize impacts to a mammalian head. The term "head" is used herein to indicate any portion of the cranium, brain, maxilla, mandible and mouth structures (e.g., teeth), occipito-cervical region, low cervical region (C5, C6, and C7 vertebrae), and associated portions of the spinal cord, as well as any other head and neck structures which could be adversely effected by a directly applied and/or a transmitted (e.g., head snaps back after a body tackle) impact force. The system 50 includes one or more sensor assemblies 52 positioned in the vicinity of the head. In accordance with an aspect of the present invention, each sensor assembly 52 is configured to measure at least one of the linear acceleration, angular velocity, angular acceleration, and orientation of the sensor assembly 52 along any desired axis or set of orthogonal axes. In the one implementation, the sensor assemblies 52 can be implemented as MEMS (microelectromechanical systems) sensors configured to measure one or more of the linear acceleration, angular velocity, angular acceleration, and orientation of the head at the point of affixation of the sensor. It will be appreciated that the sensor assemblies 52 can be placed in any appropriate apparatus that can be fixedly mounted to or within a mammalian head, such as a helmet, a mouthpiece, a headband, eyewear, or an instrument that is inserted in the auditory canal, mounted in the nasal canal, or affixed to the skin In one implementation, the sensor assemblies 52 can be mounted with a mouthpiece apparatus. Here, a mouthpiece may be a dental/orthodontic appliance (e.g., retainer), mouthguard, dental implant (e.g., prosthetic tooth), or any other suitable device located, temporarily or permanently, within a user's oral cavity. In accordance with an aspect of the present invention, it has been determined that the use of a mouthpiece provides several advantages. To begin with, many helmeted (e.g., football, military, hockey, lacrosse, amateur boxing, wrestling, motocross, bicycling) and non-helmeted (e.g., basketball, professional boxing and mixed martial arts, soccer, field hockey, rugby, Australian Football, multisport, golf) activities already utilize a protective or vanity mouthpiece, which may facilitate quick acceptance and general usage of the described sensing mouthpiece assembly. Further, a firm coupling between the sensors associated with the mouthpiece apparatus and the head is achieved from tight fitting between the teeth and mouthpiece substrate material, surface tension provided by saliva and bolstered by jaw clenching during activity or in response to impending impact. A mouthpiece implementation, particularly in combination with the daisy-chain registration process described herein, has been shown to provide a high degree of kinematic and kinetic calculation accuracy while using a device that is of a format already familiar to, and accepted by, participants in the recreation, military, or other mouthpiece-using activity.

The mouthpiece can be formed from any appropriate material for absorbing shock between the maxilla (upper jaw) and mandible (lower jaw) and/or material designed to induce cervical spine muscle activation in response to impending head impact while having sufficient flexibility to conform to the mouth and contain the sensor assemblies 52. The sensor assemblies 52 may be encapsulated entirely by surrounding material of the mouthpiece, embedded partially in the material (e.g., a substrate), and/or placed in non-surrounding contact with the material (e.g., attached to a surface of a mouthpiece). In one implementation, the mouthpiece is formed from multiple layers of material, with one layer including a sensors mounted, for example in an elongate pattern. This allows for quick insertion/removal of the sensor assemblies 52 and allows worn out parts to be replaced. The sensor strip can comprise a plurality of MEMS-based linear and rotational kinematic sensors.

In an exemplary implementation, the sensor strip includes six embedded linear accelerometers, three embedded angular velocity sensors, and three embedded tilt sensors. It will be appreciated, however, that this sensor configuration is merely given for the purpose of example, and implementations using just an array of linear accelerometers or just an array of angular velocity/angular acceleration sensors are also envisioned. Essentially, any appropriate combination of linear accelerometers, angular accelerometers, angular velocity sensors, or orientation sensors can be utilized in accordance with an aspect of the present invention. The linear accelerometers are capable of measuring linear acceleration up to two thousand times the standard gravitational acceleration, the angular velocity sensors are configured to measure angular velocity up to one hundred radians per second, far exceeding typical athlete head impacts of one or two hundred times the standard gravitational acceleration, the angular accelerometers are capable of measuring angular acceleration up to fifty thousand radians per second squared, and the orientation sensors are configured to measure position in space over a full three hundred sixty degree arc. Each sensor footprint occupies a volume of roughly four millimeters by four millimeters by two millimeters.

It will be appreciated that, in accordance with an aspect of the present invention, because of the generic nature of the algorithm used to calculate localized head kinematics and kinetics, the placement and number of the sensors can be essentially arbitrary, such that no specific relationship among the positions or type of the plurality of sensors is required. Each sensor assembly 52 is positioned at a known location on an associated apparatus, such that the position of the sensor relative to a designated origin of an apparatus reference frame is known to the system 50. The mouthpiece can further include a component for wireless data transmission to allow the sensor data to be provided to an external processor. For example, the mouthpiece can include a radio frequency (RF) or microwave transmitter operating with an appropriate transmission protocol and a miniature antenna, or high- or low-power Bluetooth digital data transmission protocol.

To facilitate capture and transfer of the data, the mouthpiece can include a flash memory accessible in a wired or wireless manner. For example, a port can be provided on the mouthpiece to allow data to be transferred to a computer via a universal serial bus (USB) or other connection. The sensors and the transmitter can be powered by an on-board battery, which can be shaped to fit the contour of the mouthpiece. It will be appreciated that the mouthpiece can include physiochemical sensors to monitor internal body metrics such as, but not limited to, temperature, hydration, pH, glucose level, sodium concentration, oxygen saturation, troponin, and respiration.

In accordance with an aspect of the present invention, the data collected by the sensors can be provided to a data transform component 54 configured to calculate the kinematics and kinetics at any location of the head, including the center of gravity of the head. It will be appreciated that the data transform component 54 can be implemented as dedicated hardware, software executed on a general purpose processor, or some combination of dedicated hardware and software. Further, the data transform component 54 can be implemented on a platform associated with the sensors (e.g., a mouthpiece or helmet), in a processing unit worn by the player, either hardwired or wirelessly connected to the sensor assembly, at a remote location, or distributed across multiple discrete processing components. One or more of linear acceleration, angular acceleration, angular velocity and orientation are measured at the sensor assemblies, and data derived from the daisy-chain registration process and, optionally, head anthropometry can be used to calculate corresponding linear and angular head kinetics and kinematics at any location of the head. For example, the position of each sensor assembly 52 relative to the location defining the center of gravity of the head can be determined and registered at the data transform component 54.

In one implementation, the desired calculation location can be represented as a static location during the impact, and translation of the sensor data at the data transform component 54 can be accomplished according to the following "rigid body" relationship between the measured kinematics at a sensor, $\tilde{\alpha}_{mouth}(t)$, $\tilde{\omega}(t)$ $\tilde{\alpha}(t)$ and the acceleration at the desired location, $\tilde{\alpha}_{LOC}(t)$:

$$\tilde{\alpha}_{LOC}(t) = \tilde{\alpha}_{mouth}(t) + \tilde{\omega}(t) \times (\tilde{\omega}(t) \times \tilde{\rho}) + \tilde{\alpha}(t) \times \tilde{\rho} \qquad \text{Eq. 1}$$

where $\tilde{\omega}(t)$ is the three dimensional measured or calculated angular velocity of the head, $\tilde{\alpha}(t)$ is the three dimensional measured or calculated angular acceleration of the head and $\tilde{\rho}$ is a three dimensional displacement between the sensor and the desired location within the head determined from the registration process.

In accordance with an aspect of the present invention, the position of each sensor assembly relative to any desired location, including the center of gravity, of the head can be represented as a time-varying function. In any significant impact, the brain will move around in the skull, such that the tissue located at the desired location, including center of gravity, of the head varies for a period of time after the impact. Accordingly, the relative location can be expressed as a function of the kinematic values measured at the sensors as well as the measured head anthropometry. In accordance with an aspect of the present invention, the data transform component 54 can incorporate a model of the movement of the brain, given a set of anthropometric parameters describing the head, when exposed to various kinematics and kinetics, including linear acceleration, angular acceleration, angular velocity, orientation change, impact force and energy absorption among others. For example, a desired location can be represented as a plurality of time-varying functions, with a given function selected according to the kinematic values measured at the sensor assembly 52. By tracking the actual center of gravity of the head throughout the movement induced by the impact, the linear acceleration, angular acceleration, angular velocity, and orientation changes experienced at the brain, and the corresponding physiological effects, can be calculated more accurately via this "deformable body" approach.

In this implementation, translation of the sensor data at the data transform component 54 can be accomplished according to the following relationship between the acceleration at a sensor, $\tilde{\alpha}_{mouth}(t)$, and the acceleration at the desired location, in this case assumed to be center of gravity, $\tilde{\alpha}_{CG}(t)$:

$$\tilde{\alpha}_{CG}(t) = \tilde{\alpha}_{mouth}(t) + \tilde{\omega}(t) \times (\tilde{\omega}(t) \times \tilde{\rho}(t)) + \tilde{\alpha}(t) \times \tilde{\rho}(t) + \ddot{\tilde{\rho}}_r(t) + 2\tilde{\omega}(t) \times \dot{\tilde{\rho}}_r(t) \qquad \text{Eq. 2}$$

where $\tilde{\omega}(t)$ is the three dimensional measured or calculated angular velocity of the head, $\tilde{\alpha}(t)$ is the three dimensional measured or calculated angular acceleration of the head, $\tilde{\rho}(t)$, $\dot{\tilde{\rho}}_r(t)$ and $\ddot{\tilde{\rho}}_r(t)$ are functions representing time-varying three dimensional displacement, velocity and acceleration, respectively between the sensor and the desired location (i.e., at the center of gravity) within the head and determined from the head anthropometry, the registration process, and the kinematic data measured at the sensors.

The calculated kinematics and kinetics at the desired location, including acceleration at the desired location (i.e., at center of gravity) of the head is provided to a system interface 56, where the information is provided to an observer in a human comprehensible form. For example, the kinematic and kinetic values associated with a head impact and the various measured physiological parameters of a user in real time can be shown to an observer at an associated display. The measured data can, for instance, be used to score a boxing or mixed martial arts (MMA) competition or provide supplementary content to enrich the fan experience in person or remotely. To enhance the safety of these events or other events likely to produce significant impacts to the head and neck, the measured and calculated kinematic and kinetic data can be displayed to an observer and/or trigger one or more remote warning devices when a user exceeds a critical head impact or physiological threshold. Where practical, the sensor data can be used to activate an associated intervention system, human or automated, to prevent injury to the user. The system interface 56 can also provide quantitative measures for correlation with post-event neurological assessment, including physical exams, blood exams, genetic typing, and imaging modalities such as coherence tomography, magnetic resonance imaging, diffusion tensor imaging, and positron emission tomography. It is believed that an individual's susceptibility to many neurocognitive disorders later in life can be enhanced even by repeated minor impacts to the head. Accordingly, the system interface 56 can be configured to tabulate head impact cumulatively, such as during training or over the course of an athlete's career, as a guide to prevention of long-term neurocognitive disorders, including Parkinson's disease, loss of memory, dementia pugilistica, second impact syndrome, psychiatric disorders, and Alzheimer's disease.

Figure 4:
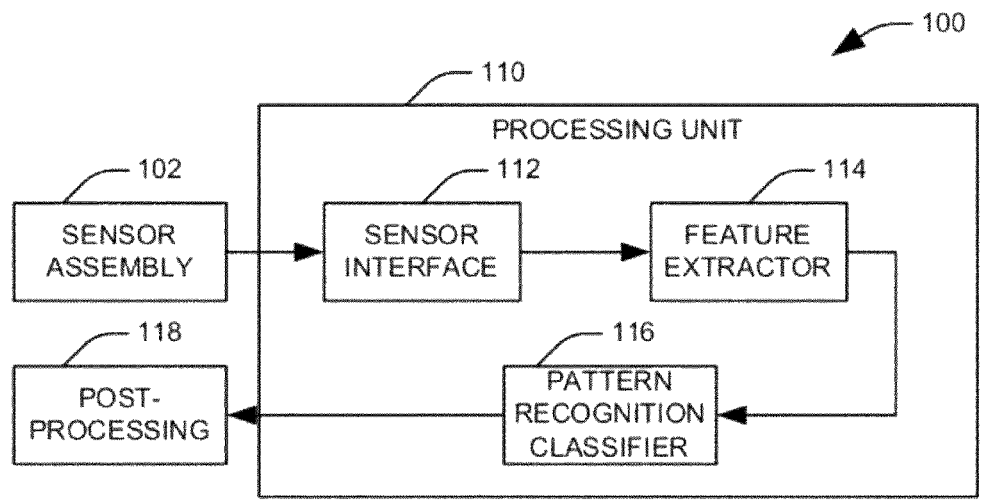
FIG. 4 illustrates a classification system for classifying an impact into an associated event class.

FIG. 4 illustrates a classification system 100 in accordance with an aspect of the present invention. The classification system 100 comprises at least one sensor assembly 102 deployed as to be substantially fixedly engaged with a human head. In the illustrated implementation, the sensor assembly 102 is engaged with the head of a participant in an athletic event, for example, as part of a mouthpiece or on a surface of a helmet, though any suitable substantially fixed engagement may be used. For example, the sensor assembly 102 could also or instead be stuck to the skin surface, inserted into the nasal cavity, located in one or more of a replacement tooth implant, an auditory canal implant, a helmet liner, a headband, and eyewear, or even directly attached to the head via a skull anchor or the like. The sensor assembly 102 is operative to measure the kinematics of the head along any desired axis, including three mutually orthogonal axes, at the location of the sensor as well as the angular acceleration, angular velocity, and orientation of the head about any coincident or non-coincident axis or set of axes.

In accordance with an aspect of the present invention, the classification system 100 is configured to measure the kinematics induced by an impact to the head monitored by the sensor assembly 102 and categorize the impact as one of a plurality of event classes via calculated kinematics and kinetics at any desired location on the head. In one implementation, the various event classes can correspond to ranges of likelihood for various head and neck injuries given the measured impact. It will be appreciated that training data for a classifier system can be initially derived from cadaver studies, animal studies, and/or computer or mechanical simulations and refined with data collected during usage of the device. For example, a first set of classes could represent ranges of probabilities of a concussion given the measured impact, a second set of classes could represent ranges of probabilities of a skull fracture given the measured impact, and a third set of classes could represent ranges of probabilities of neck injury given the measured impact. From the determined class, an observer, such as a coach or trainer, can make decisions about a user's, such as an athlete's, further participation in an event or the desirability of additional protective and/or diagnostic measures. Further, the determined event class can provide an instantaneous on-site or off-site triage tool for a physician in diagnosing and treating a potential injury to the head or neck arising from the measured impact.

In another implementation, the various event classes can represent an origin or associated type of the impact. For example, where the athletic event is a boxing match, the various event classes could represent a hook, an oblique hook, a jab to the forehead or face, an uppercut, a cross, or an overhand punch. The classes could be further refined to identify the type and handedness of a punch. In an MMA match, the classes could be further expanded to include various kicks as well as the impact of elbows and knees to the head. For American football, the type and severity of contact (e.g., helmet-helmet, helmet-knee, helmet-ground) can be ascertained. For soccer, head-head contacts can be delineated from head-elbow or head-goalpost impacts. Such information could be utilized for scoring purposes, possibly by being provided to a graphical user interface for "instant replay" as well as for summarizing the action of a match for later review. Further, in accordance with an aspect of the present invention, the event class information can be used to provide a computer simulation of the match, for example, to enhance the viewing experience for spectators or to drive advanced finite element models of brain injury.

To this end, the sensor data is provided to a processing component 110 configured to provide a human comprehensible output from the sensor data. A sensor interface 112 is configured to determine kinematics and kinetics, including a linear acceleration, at the desired location from the sensor data. It will be appreciated that the transform of the kinematics data from the sensor to provide kinematic and kinetic data at the desired location can be performed either by assuming a static tissue location, referred to herein as a 'rigid body' analysis, or with a dynamic tissue location represented by a time-varying function, referred to herein as a 'deformable body' analysis.

The transformed sensor data is then provided to a feature extractor 114 that extracts a plurality of features from the transformed data. In accordance with an aspect of the present invention, the plurality of features can be selected to include at least one feature that is a function of the kinematics and/or kinetics of the head at the desired location.

One set of parameters that are useful as classification features can be derived as functions of the linear acceleration of the center of gravity of the head. For example, a magnitude of the acceleration at the center of gravity can be determined from the acceleration along each of the three coordinate axes, and a resultant jerk at the center of gravity can be calculated as the time derivative of the magnitude of the acceleration. Similarly, a direction of the acceleration can be determined from the acceleration along each axis. The change in the velocity of the head in a given direction, or delta-V, can be determined by integrating the determined acceleration of the center of gravity of the head along that direction, and a corresponding linear momentum can be determined as the product of the change in velocity and a mass of the head, which can be estimated from head anthropometry. Similarly, a kinetic energy of the head can be determined as one-half the product of the mass of the head and the square of the change in velocity, and a power imparted to the head can be determined as the time derivative of the kinetic energy.

Several additional metrics can be derived from the measured and calculated linear acceleration values, such as an impact force along each axis, calculated as the product of the mass of the head and the acceleration at the center of mass along each axis, and a magnitude of the impact force. A loading rate can be determined as the time derivative of the impact force, and minimum and maximum values of this loading rate can be utilized as features. A duration of the impact can be calculated based on the length of the loading and unloading pulse after initial contact as based on impact force.

A value representing the Gadd Severity Index (GSI) can be calculated as:

$$GSI = \int_0^T \tilde{a}_R(t)^{2.5} dt \qquad \text{Eq. 3}$$

where $\tilde{a}_R(t)$ is the resultant magnitude of the calculated linear acceleration at the center of gravity expressed as a multiple of the standard gravitational acceleration at Earth's surface (g=9.81 m/s$^2$), and the period [0:T] is an essential impact duration. In one implementation, this duration is selected to be fifteen milliseconds.

A value for the Head Injury Criterion (HIC) can be calculated as:

$$HIC = (t_2 - t_1)\left[\frac{1}{t_2 - t_1}\int_{t1}^{t2} \tilde{a}_R(t) dt\right]^{2.5} \qquad \text{Eq. 4}$$

where $\tilde{a}_R(t)$ is the resultant magnitude of the calculated linear acceleration at the center of gravity expressed as a multiple of the standard gravitational acceleration and the period [t$_1$:t$_2$] is a time period for which the HIC is maximized, referred to as the HIC duration. In one implementation, the HIC duration, equal to $t_2-t_1$, can also be utilized as a classification feature.

A Skull Fracture Correlate (SFC) value can be calculated as:

$$SFC = \left[ \frac{\max(\text{Delta} - V_R(t))}{\text{HIC Duration}} \right] \frac{1}{g} \quad \text{Eq. 5}$$

where g is standard gravitational acceleration and Delta-$V_R(t)$ is the resultant change in velocity of the head.

A second set of parameters useful for event classification are derived as functions of the angular velocity and angular acceleration of the head. For example, a magnitude of the angular acceleration can be determined from the acceleration about each of the three coordinate axes, and a magnitude of the angular velocity can be determined from the velocity about each of the three coordinate axes. A jerk resulting from the angular acceleration can be calculated as the time derivative of the magnitude of the angular acceleration. A head angular momentum can be determined from the angular velocity about each axis and a corresponding moment of inertia. The moments of inertia can be estimated from the head anthropometry. A magnitude of the angular momentum can be determined from the angular momentum about each of the three coordinate axes.

A Generalized Acceleration Model for Brain Injury Threshold (GAMBIT) can be calculated as:

$$GAMBIT(t) = \left[ \left( \frac{\tilde{a}_R(t)}{\tilde{a}_C} \right)^{2.5} + \left( \frac{\tilde{\alpha}_R(t)}{\tilde{\alpha}_C} \right)^{2.5} \right]^{\frac{1}{2.5}} \quad \text{Eq. 6}$$

where $\tilde{\alpha}_R(t)$ is the resultant magnitude of the linear acceleration at the center of gravity expressed as a multiple of the standard gravitational acceleration, $\tilde{\alpha}_C$ is a critical linear acceleration equal to two hundred fifty times the standard gravitation acceleration, $\tilde{\alpha}_R(t)$ is a resultant magnitude of the angular acceleration, and $\tilde{\alpha}_C$ is a critical angular acceleration equal to twenty-five thousand radians per second.

A Weighted Principal Component Score (wPCS) can be calculated as:

$$wPCS = \quad \text{Eq. 7}$$
$$k_{lat} \times 10 \left( \left[ \begin{array}{c} k_{GSI}\left(\frac{GSI - GSI_m}{GSI_{sd}}\right) + k_{HIC}\left(\frac{HIC - HIC_m}{HIC_{sd}}\right) + \\ k_{LIN}\left(\frac{\max(\tilde{a}_R(t)) - a_m}{a_{sd}}\right) + k_{ROT}\left(\frac{\max(\tilde{\alpha}_R(t)) - \alpha_m}{\alpha_{sd}}\right) \end{array} \right] + 2 \right)$$

where is $k_{lat}$ is a weight with a value of 1 for a lateral impact, $k_{GSI}$ is a weight with a value of 0.4718, $k_{HIC}$ is a weight with a value of 0.4720, $k_{LIN}$ is a weight with a value of 0.4336, $k_{ROT}$ is a weight with a value of 0.2164, $HIC_m$ is a mean value of the HIC over a plurality of sample impacts, $HIC_{sd}$ is a standard deviation of the HIC over the plurality of sample impacts, $GSI_m$ is a mean value of the GSI, $GSI_{sd}$ is a standard deviation of the GSI, $a_m$ is a mean value of the linear acceleration at the center of gravity, $a_{sd}$ is a standard deviation of the linear acceleration at the center of gravity.

A Head Impact Power (HIP) can be calculated as:

$$HIP = m_{head}\left[ \tilde{a}_{CGX}(t)\int \tilde{a}_{CGX}(t)dt + \right. \quad \text{Eq. 8}$$
$$\tilde{a}_{CGY}(t)\int \tilde{a}_{CGY}(t)dt + \tilde{a}_{CGZ}(t)\int \tilde{a}_{CGZ}(t)dt \right] + +$$
$$I_X \tilde{\alpha}_X(t)\int \tilde{\alpha}_X(t) + I_Y \tilde{\alpha}_Y(t)\int \tilde{\alpha}_Y(t) + I_Z \tilde{\alpha}_Z(t)\int \tilde{\alpha}_Z(t)$$

where $m_{head}$ is a mass of the head, determined from anthropometric data, $\tilde{a}_{CGX}$ is an acceleration at the center of gravity along a anterior-posterior axis, $\tilde{a}_{CGY}$ is an acceleration at the center of gravity along a lateral axis, $\tilde{a}_{CGZ}$ is an acceleration at the center of gravity along an cranio-caudal axis, $\tilde{\alpha}_X$ is an angular acceleration about a anterior-posterior axis, $\tilde{\alpha}_Y$ is an angular acceleration about a lateral axis, $\tilde{\alpha}_Z$ is an angular acceleration about an cranio-caudal axis, $I_X$ is a head mass moment of inertia about a anterior-posterior axis, $I_Y$ is a head mass moment of inertia about a lateral axis, and $I_Z$ is a head mass moment of inertia about an cranio-caudal axis.

A number of additional features can be determined by modeling the measured impact in a finite element model of the brain. For example, features can be generated corresponding to percentages of the volume of the brain experiencing various levels of principle strain. In the illustrated implementation, each of a first percentage of the brain volume experiencing a principal strain exceeding five percent, a second percentage of the brain volume experiencing a principal strain exceeding ten percent, and a third percentage of the brain volume experiencing a principal strain exceeding fifteen percent can be used as features. Similarly, a dilation damage measure (DDM) can be calculated from the model as a percentage of brain volume experiencing a negative pressure less than 101.4 kilopascals. A relative motion damage measure (RMDM) can be calculated as:

$$RMDM = \frac{\varepsilon(t)}{\varepsilon_F(t, \dot{\varepsilon}(t))} \quad \text{Eq. 9}$$

where $\epsilon(t)$ is a bridging vein strain, as determined by the finite element model, and $\epsilon_F(t, \dot{\epsilon}(t))$ is a strain associated with bridging vein failure at a given strain rate, as determined by the finite element model.

Similarly, a possibility of neck injuries can be accessed via a calculated force at the occipital-cervical junction along each axis and a determined occipital moment about each axis, as well as a magnitude of the force and the occipital moment. A Neck Injury Criterion ($N_{ij}$) can be calculated as:

$$N_{ij} = \max\left[ \frac{\tilde{F}_{occZ}(t)}{F_{Zcrit}} + \left( \frac{\tilde{F}_{occY}(t)*d + \tilde{M}_{occX}}{M_{Xcrit}} \right) \right] \quad \text{Eq. 10}$$

where $\tilde{F}_{occZ}(t)$ is the occipital force along an cranio-caudal axis, $\tilde{F}_{occY}(t)$ $\tilde{F}_{occY}(t)$ is the occipital force along a lateral axis, $\tilde{M}_{occX}$ is the occipital moment about a anterior-posterior axis, $F_{Zcrit}$ is a critical occipital axial force equal to 6806 Newtons, $M_{Xcrit}$ is a critical occipital moment equal to one hundred thirty-five Newton-meters, and d is a distance equal to 0.01778 meters.

The calculated features are then provided to a pattern recognition classifier that selects an event class representing the impact from a plurality of event classes. The pattern recognition classifier 116 can utilize any of a number of classification techniques to select an appropriate event class from the plurality of numerical features. Further, the pattern recognition classifier 116 can utilize features that are not derived from the sensor data, such as an age, height, or weight of the user and one or more numerical parameters derived from a medical history of the user, such as a recorded history of previous sensed or reported head impacts. In one implementation, the pattern recognition classifier 116 comprises a rule based classifier that determines an event class according to a set of logical rules. Alternatively, the pattern recognition classifier 116 can comprise a Support Vector Machine (SVM) algorithm or an artificial neural network (ANN) learning algorithm to determine an occupant class for the candidate occupant. A SVM classifier can utilize a plurality of functions, referred to as hyperplanes, to conceptually divide boundaries in an N-dimensional feature space, where each of the N dimensions represents one feature provided to the SVM classifier. The boundaries define a range of feature values associated with each class. Accordingly, an output class can be determined for a given input according to its position in feature space relative to the boundaries.

An ANN classifier comprises a plurality of nodes having a plurality of interconnections. The feature values are provided to a plurality of input nodes. The input nodes each provide these input values to layers of one or more intermediate nodes. A given intermediate node receives one or more values from previous nodes. The received values are weighted according to a series of weights established during the training of the classifier. An intermediate node translates its received values into a single output according to a transfer function at the node. For example, the intermediate node can sum the received values and subject the sum to a binary step function. These outputs can in turn be provided to additional intermediate layers, until an output layer is reached. The output layer comprises a plurality of outputs, representing the output classes of the system. The output class having the best value (e.g., largest, smallest, or closest to a target value) is selected as the output class for the system.

The selected event class is provided to a post-processing component 118 configured to provide the event class to a human operator in a human comprehensible form. This can comprise a display that simply displays a label associated with the class, a computer simulation, or even a simple auditory or visual indicator that alerts an observer than a user may have sustained an impact that falls within the selected event class.

In view of the foregoing structural and functional features described above, a methodology in accordance with various aspects of the present invention will be better appreciated with reference to FIGS. 5-9. While, for purposes of simplicity of explanation, the methodologies of FIGS. 5-9 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

Figure 5:
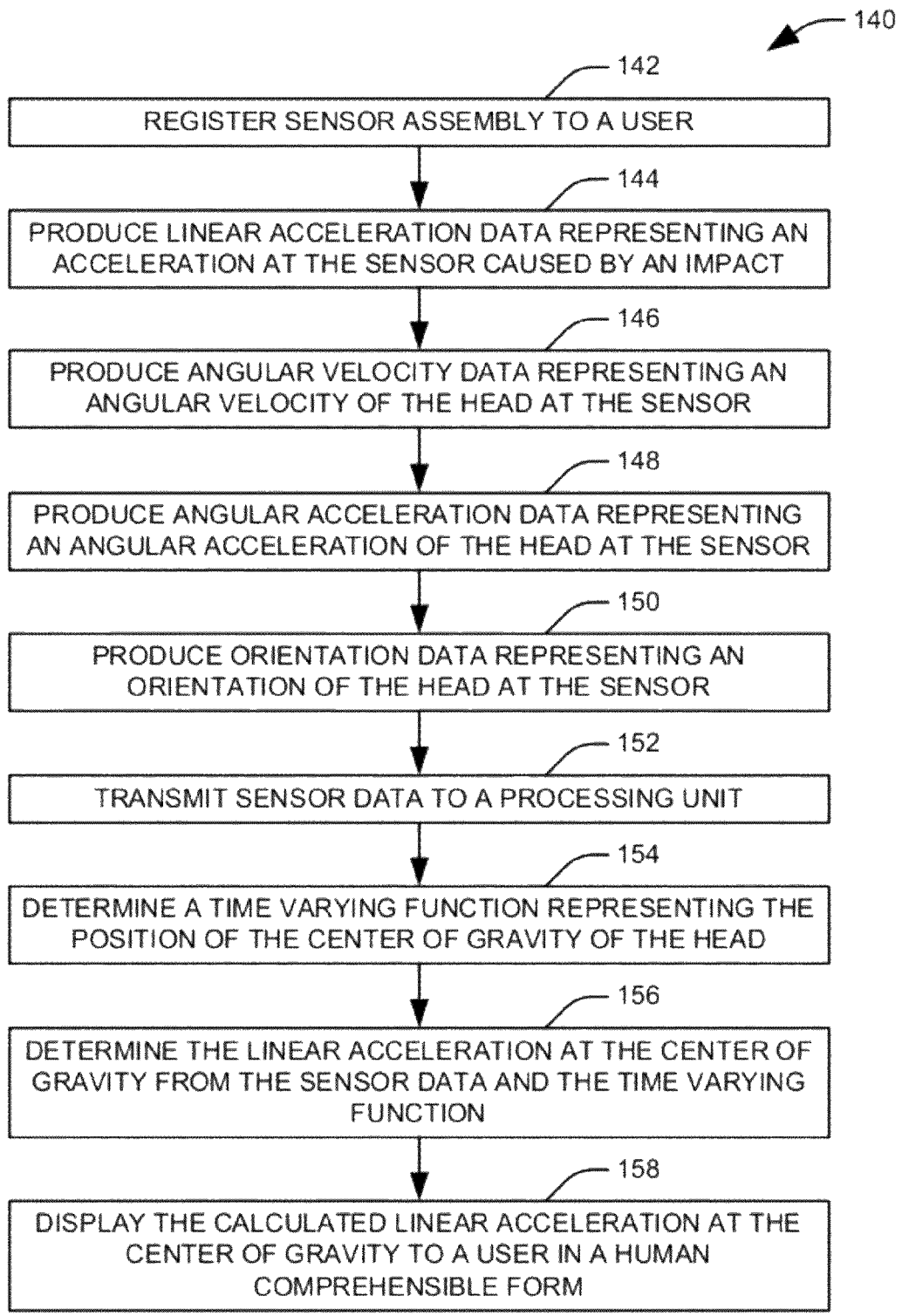
FIG. 5 illustrates one example of a method for determining kinematics and kinetics at a center of gravity, or any other point, within a user's head.

FIG. 5 illustrates one example of a method 140 for determining kinematics and kinetics at an arbitrary location within the head in accordance with an aspect of the present invention. For the purpose of example, this method describes determining kinematics and kinetics at a center of gravity of a user's head, as it has been determined, in accordance with an aspect of the present invention, kinematic and kinetic data at the center of gravity is a useful predictor in classifying head impact events. The method begins at 142, where a sensor assembly is initialized for use for a given user and attached to the user's head in a substantially rigid manner to an ambient-accessible surface of the user's head (e.g., in a mouthpiece or implant within the auditory canal). For example, various measurements of the user's head can be taken and one or more values or time varying functions representing a center of gravity of the head of that user, relative to an external anatomical landmark, can be determined.

In an implementation using a mouthpiece assembly, a "daisy-chain" registration process can be used, in which the position and orientation of the sensor with respect to reference point on the mouthpiece, such as a breakaway tab or other easily accessible location near the lips, is determined. The position of the reference point on the mouthpiece is then determined relative to an external anatomical landmark of the user, such as external auditory meatus, tragus, orbital rim, or similar anatomical structure. The location of the external anatomical landmark location is then estimated relative to a center of gravity, or any other desired point, within the head, and this estimate is then used to determine the position of the sensor relative to the center of gravity or other desired point to complete the registration process.

At 144, linear acceleration data is produced from the sensor assembly, representing acceleration experienced by the user's head at the site of the at least one sensing device. In one implementation, the sensor assembly is configured to be responsive only to impacts producing a predetermined acceleration, such that impacts below a threshold acceleration are not stored or transmitted. The sensor assembly can be configured to conserve power in a sleep mode, with the sensors only powered fully when collecting data in bursts. It will be appreciated that the sensor assembly can include one or more signal conditioning elements configured to take raw voltage data from sensors and convert to an appropriate signal for storage or transmission. For example, the signal conditioning elements can include one or more amplifiers, integrators, filters, and multiplexers for providing a coherent signal for one or both of transmission and storage. At 146, angular velocity data indicative of an angular velocity of the user's head is provided by the sensor assembly. At 148, angular acceleration data indicative of an angular acceleration of the user's head is provided by the sensor assembly. At 150, orientation data indicative of an orientation of the user's head is provided by the sensor assembly.

At 152, the sensor data is transmitted to a processing component, for example, via a wired or RF wireless connection, such as a Bluetooth connection. At 154, a location of the center of gravity of the user's head relative to a position of the at least one sensing device is determined as a function of time from the registered location data and the sensor data. For example, the processing unit can comprise a look-up table containing various time varying functions representing the position of the center of gravity, and a given function can be selected according to associated ranges of linear acceleration, angular velocity, angular acceleration and orientation data measured.

At 156, the acceleration at the center of gravity of the user's head is calculated as a function of the sensor data, the represented location of the center of gravity of the user's head, the angular velocity data, the angular acceleration data, and the orientation data. At 158, the calculated kinematic and kinetic data are then provided to at least one of the user and an observer in a human-perceptible form. For example, the mouthpiece could be configured to provide any or all of an auditory, a visual, and a tactile stimulus to the user and/or an observer in response to an impact producing a dangerous level of acceleration. Alternatively, the calculated kinematic and kinetic data can be provided to an observer at an associated display.

FIG. 6 illustrates a methodology 170 for classifying an impact into an event class in accordance with an aspect of the present invention. At 172, at least one of linear acceleration data, angular velocity data, angular acceleration data, and orientation data are acquired from a sensor assembly. For example, the sensor assembly can include one or more of a plurality of linear accelerometers, a plurality of angular velocity sensors, and a plurality of orientation sensors. An angular acceleration can be determined from the angular velocity. At 174, the sensor data is conditioned to enhance the raw sensor data, eliminate obvious noise, and otherwise prepare the sensor data for further processing. At 176, the conditioned sensor data and known anthropometric parameters of a user are used to calculate the linear and rotational kinematics and kinetics at the center of gravity of the head.

At 178, a plurality of features are extracted from the sensor data. In accordance with an aspect of the present invention, a subset of at least two of the plurality of features can be derived from the calculated kinematics and kinetics at the center of gravity of the head. In addition, the plurality of features can include an age, height, or weight of the user as well as one or more numerical parameters derived from a medical history of the user. The extracted features represent the circumstances of the impact as a vector of numerical measurements, referred to as a feature vector. At 180, the feature vector is related to a most likely event class, based on an appropriate classification technique. For example, the feature vector can be classified via a series of logical rules at an appropriate rule-based expert system. Alternatively, the classification can be performed by a statistical or neural network classifier. In one implementation, the classification technique further provides a confidence value representing the likelihood that the pattern is a member of the selected event class. The confidence value provides an external ability to assess the correctness of the classification. For example, a classifier output may have a value between zero and one, with one representing a maximum certainty.

At 182, the selected event class is conveyed to the user or an observer in a human comprehensible form. For example, a label associated with the class can be displayed, a computer simulation can be generated to represent the selected event, or an auditory or visual indicator can alert an observer, such as a coach or trainer, when an event class representing a danger to the user is selected. Where a confidence value is generated, it can also be provided to the observer to aid in decisions as to the user's further participation in the event or to aid in any medical diagnosis.

Figure 7:
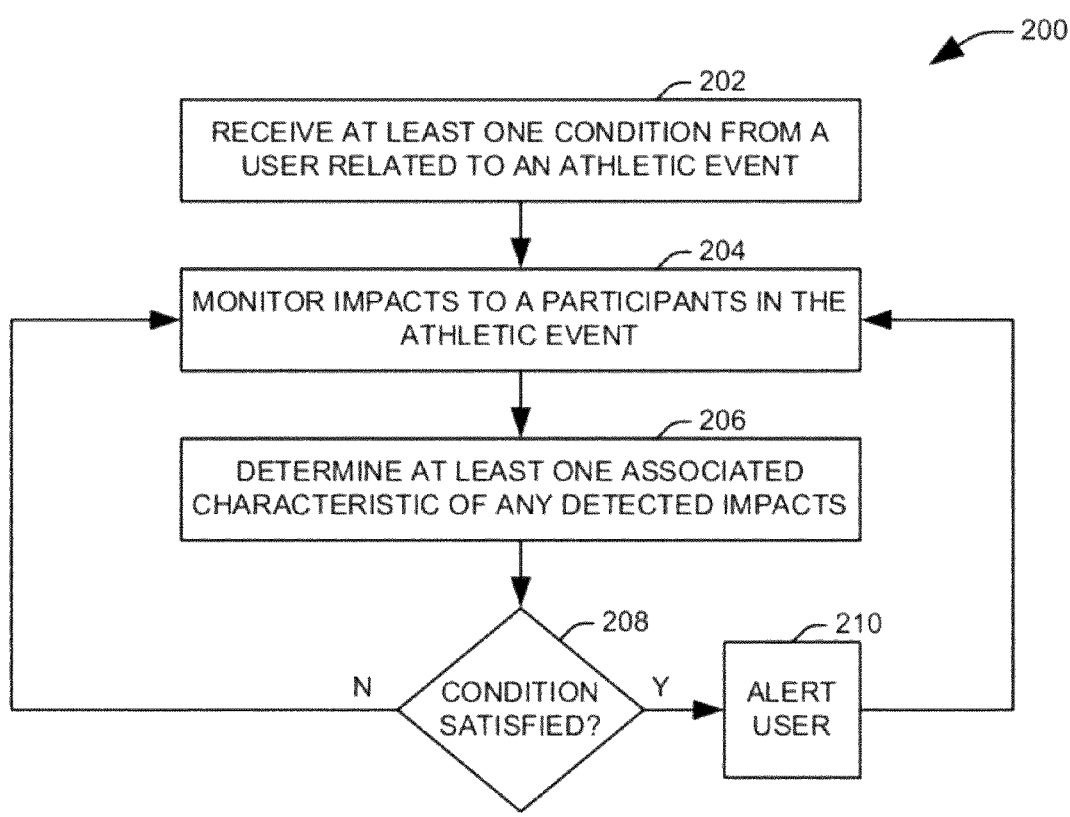
FIG. 7 illustrates a methodology for utilizing an impact monitoring system to augment the experience of a non-participant of an athletic event.

FIG. 7 illustrates a methodology 200 for utilizing an impact monitoring system in accordance with an aspect of the present invention to augment the experience of a non-participant of an athletic event. At 202, at least one condition, related to the athletic event, is provided by a non-participating user and received at the impact monitoring system. For example, the at least one condition can be provided to an system interface of the impact monitoring system, such that the various impacts received or delivered by individuals outfitted with the sensor assemblies described previously can be compared to the defined conditions.

It will be appreciated that the at least one condition can vary with the desired application. For example, a condition can relate to an impact received by a specific participant, such as an impact having a linear acceleration at the center of gravity of the head greater than a threshold value occurring to a specified participant or an impact that falls within a particular event class (e.g., a helmet-to-helmet impact in American football). The condition could be as simple as the occurrence of any significant impact to a participant's head. It will be appreciated that the condition does not need to be specific to a particular impact, and could represent, for example, a threshold for a cumulative force or acceleration experienced by a given participant. Alternatively, a condition can include the detection of a specific event class, such as a particular impact source. For example, in a boxing match, the condition can be the occurrence of a particular kind of punch or a punch producing a force or imposed acceleration above a threshold value.

At 204, impacts to participants in the athletic event are monitored. At 206, at least one characteristic is determined for any detected impacts. The determined characteristic can include a magnitude of a given impact, an associated location of the impact, or an event class of the impact, such as an impact source, a "legal/illegal" hit determination, or a likelihood of injury represented by the impact. At 208, it is determined if any of the defined conditions are satisfied by the determined characteristic. If not (N), the methodology 200 returns to 202 to continue monitoring for impacts. If so (Y), a user is altered that the condition has been satisfied at 210, and the methodology 200 returns to 202 to continue monitoring for impacts.

It will be appreciated that the method of FIG. 7 can be used for any of a number of purposes. In one example, the non-participant can be a parent, coach, official or other person with a direct interest in the well-being of a participant, and the condition can be any impact to the head of the participant or any impact to the participant's head above a threshold level of force or acceleration.

As athletes are becoming faster and regulations are becoming more complex, it has become increasingly difficult for referees to correctly enforce rules of play. This difficult task is made harder by accusations of bias in enforcing these rules. Currently, the majority of rules are enforced based on the subjective observations of the referees. To provide officials with an objective source of data to aid in rule implementation, the condition can be defined as the receipt or initiation of various types of impacts. This information could be used to provide objective scoring for various sports (e.g., boxing and mixed martial arts), or rules verification in others (e.g., detecting illegal contact to the head in American football).

The method can also be used for directly entertaining a non-participant. For example, the conditions can represent wagers placed by observers, with the determined characteristics representing a cumulative scoring total, via number or magnitude of impacts imposed or received within a region of interest. It will be appreciated that the conditions can be defined such that only impacts above a threshold magnitude are included in the scoring. Alternatively, the conditions could represent scoring categories in a fantasy sports game, for example, for boxing, American football, or mixed martial arts, with the characteristics representing various impact sources (e.g., uppercut, jab, kick, etc.), impact thresholds, and cumulative received or imposed impact totals.

Finally, an ancillary benefit of the collection of impact statistics is the ability to share the accumulated statistics with observers, both local and remote. An observer's enjoyment of the competition can be enhanced by the ability to identify the forces the player is receiving during the game. This would be even more useful to an observer with a particular interest in an individual athlete, such as a mother or father watching their son play a high school football game or an individual watching a favorite boxer during a match. The impact monitoring system can include the ability to graphically display force of impact both instantaneously and cumulatively. Similarly, a number and type of impacts exceeding a threshold force or acceleration can be displayed to the observers, along with any relevant information from any scoring performed by the system. Finally, where the system identifies the impact source and location, a computer-generated simulation of the impact can be displayed to the observer.

Figure 8:
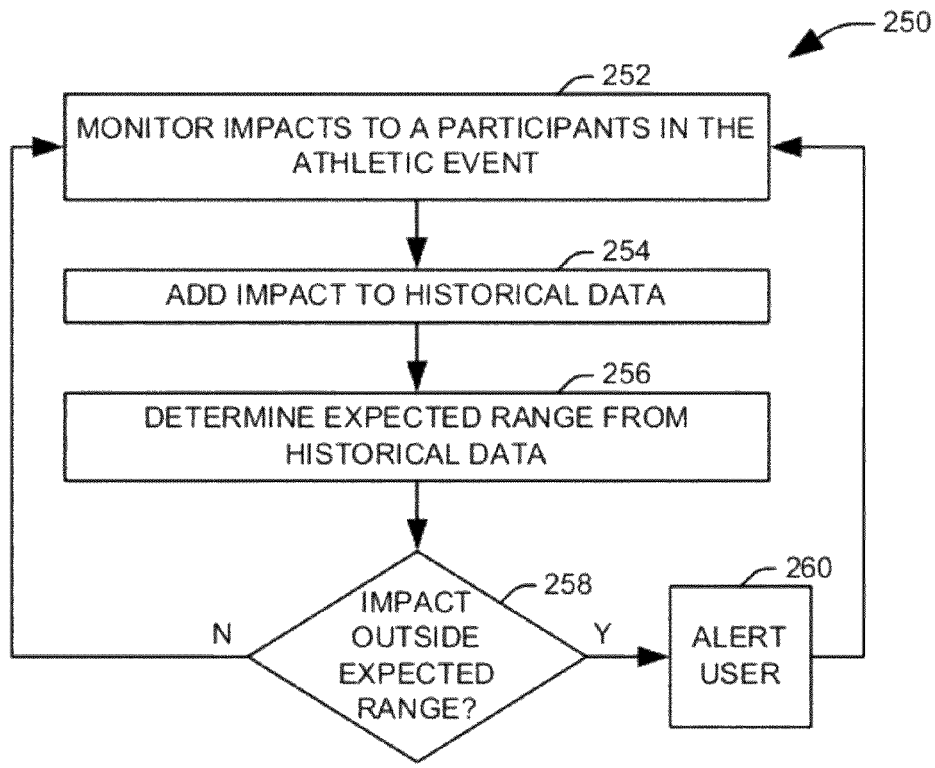
FIG. 8 illustrates a methodology for utilizing an impact monitoring system to monitor the performance and condition of an athlete in an athletic event.

FIG. 8 illustrates a methodology 250 for utilizing an impact monitoring system in accordance with an aspect of the present invention to monitor the performance and condition of an athlete in an athletic event. As technology has advanced, so have training methods for sports. In the past, it was acceptable to train based solely on non-biometric information such as distance or time of a run. It has been shown, however, that by modulating the intensity of a workout, better results can be achieved, often in a shorter time. The impact monitoring system can be a powerful aid in measuring the intensity and effectiveness of various training programs, and they can be adjusted for optimal performance improvement based on the data obtained.

One example of this would be strength training for the neck. It has long been thought that emphasizing neck strengthening could improve outcomes in athletes that receive repeated blows to the head by increasing the shock absorbing capability of the neck via its musculature. Likewise, football players that are prone to transient brachial plexus injuries (e.g., stingers/burners) or more severe injuries, such as transient quadraparesis, are often advised that intensive off-season neck strengthening would decrease the incidence of further injuries. The impact monitoring system could objectify the results of such training by capturing the amount of force received before and after training. Since the impact monitoring system can collect these measurements cumulatively, the results could be more effectively interpreted than those of a system that just measures peak impacts. For example, for training purposes, it would likely be more useful to know that an athlete has thirty percent less force acquired throughout a game than the results of any one impact. Similarly, information received by the impact monitoring system could be used to determine if a competitor is becoming less effective as the competition progresses. For example, in a boxing match, if the amount of force the opponent is receiving from a particular type of punch is declining, it could be interpreted by the observer that the athlete of interest is tiring or has a potential injury. For example, the boxer could be fatigued or have a broken hand.

Improving the athletes' technique can also prevent these injuries. To this end, the impact monitoring system data can be used to determine the effectiveness of the player's retraining in appropriate technique. Many of the newer techniques in sports are designed to minimize trauma to the head. Since these should result in decreased cumulative force registered by the impact monitoring system, it can be used to assess the effectiveness of their learning. For example, an American football player can be trained to avoid leading with the head during a tackle. Conversely, other techniques to increase the force applied to an opponent are practiced in various sports. The effectiveness of these techniques may be assessed by the impact monitoring system data from the opponent. For example, a boxer may work to improve the technique of a punch to increase force, and measure his or her progress by the increase in the force of impacts imposed on opponents. This could be made more powerful if coupled with real time video, which is now available in most competitive events.

At 252, impacts to participants in the athletic event are monitored. At 254, the force or acceleration of the measured impact is added to a library of historical data. It will be appreciated that the historical data can represent data captured over the duration of a given athletic event or training session, over the course of all or part of a season or year, or over multiple years, depending on the desired application. The historical data can be represented by a variety of descriptive statistics, including one or more of the mean, median, variance, standard deviation, interquartile range, slope, and y-intercept of the impact magnitude against time, and any other appropriate statistics. In general, the historical data will be specific to a given athlete, and only impacts associated with that athlete will be stored. It will be appreciated, however, that an impact monitoring system can store multiple libraries of historical data associated with various athletes of interest.

At 256, an expected range for impacts associated with a given athlete is determined from the historical data. For example, the expected range can be set around an average (e.g., mean or median) performance of the athlete over a given time period during or preceding an event or practice, and the range can be set around the average or another value derived from the average (e.g., the average plus or minus a desired offset value representing improvement) according to an appropriate deviation measure (e.g., standard deviation or interquartile range). Alternatively, the range can be set according to a trend line established from the historical data, to represent a continuation of observed improvement. At 258, it is determined if a given impact or averaged series of impacts delivered or received by the athlete of interest fall within the established range. If the measured impact or average is within the defined range (N), the methodology 250 returns to 252 to continue monitoring impacts. If the measured impact or average falls outside of the defined range (Y), a user, such as a coach or trainer, is altered at 260, and the methodology 250 returns to 252 to continue monitoring the athlete's status.

Figure 9:
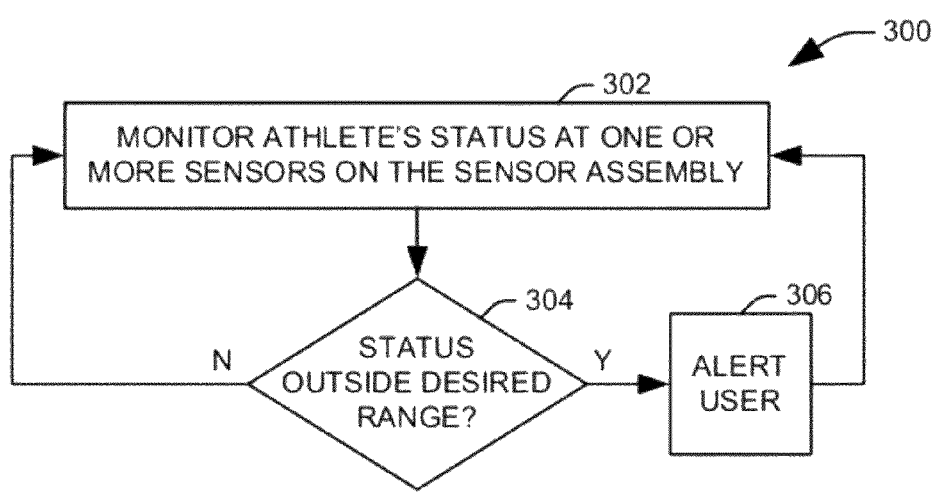
FIG. 9 illustrates a methodology for monitoring a status of an athlete during an athletic event.

FIG. 9 illustrates a methodology 300 for utilizing additional sensors, that is, sensors not directly used to measure impacts, placed on a sensor assembly in accordance with an aspect of the present invention to monitor a status of an athlete during an athletic event. At 302, a status of the athlete is detected at a sensor on the sensor assembly. For example, the sensor assembly can include one or more sensors for detecting a temperature, sodium concentration, or location associated with the user. In one implementation, the sensor assembly includes an active radio frequency identification (RFID) device that works in concert with a tracking system at a location associated with the athletic event to provide a continuous updating of each athlete's position.

At 304, it is determined if the measured status is outside of a defined range. For example, it can be determined if the temperature or sodium concentration of the athlete is outside of a normal physiological range. Alternatively, it can be determined if the athlete has left the field of play or if the athlete has ventured into a restricted region of the field of play. If the measured status is within the defined range (N), the methodology 300 returns to 302 to continue monitoring the athlete's status. If the status is outside of the defined range (Y), a user is altered of the deviation of the status from the defined range at 306, and the methodology 300 returns to 302 to continue monitoring the athlete's status.

It will be appreciated that the location tracking function of the sensor assembly could be useful in multiple contexts. It can often be difficult during team competitions to determine when a particular athlete of interest is on or off the field. A sensor assembly operating as described in FIG. 9 could give an observer an alert that their player of interest has entered the competition. For example, the parents of a high school football player could be alerted when their child is competing. The method 300 can also be used to determine where the player is at any particular time on the field of play. In one implementation, the status of the athlete could be updated regularly regardless of whether it exceeds the defined range, and a graphical interface could be provided with the position of all of the players represented by icons and the observer's player of interest having an icon of a different shape or color.

The methodology of FIG. 9 could also be used for rule enforcement. One common penalty that could be interpreted more readily with the methodology would be penalties relating to the number and position of players on the field. For example, penalties can be incurred for having too many players on the field or players at incorrect positions on the field in the sport of American football (e.g., players can be offside or too far from the line of scrimmage prior to a pass when not an eligible receiver). In one implementation, the players can be represented by icons that change color based on whether they are on or off the playing surface or according to the athlete's position on the field. This methodology could also be used by the individual team to prevent penalties.

In other applications, additional sensors placed on the sensor assembly of the impact monitoring system can be used to detect biometric data and trigger an event. Elite target shooters minimize body movement to improve accuracy. The impact monitoring system can be used as a trigger by varying pressure. It can also time the trigger to match biometrics such as heartbeat or breathing. Further, the sensor assembly can include some form of tactile indicator to improve the ability of handicapped athletes to participate. A hearing impaired athlete can be alerted to the start of an event such as a race by the transmission of a signal to the sensor assembly, with a component on the sensor assembly vibrating to alter the athlete of the starting signal. Thus, the athlete would not have to rely on vision to replace the sound of a starting signal. It would also be possible to transmit this signal to non-impaired athletes. This would allow a faster response to the start of a race versus listening for a signal and could improve performance.

Figure 10:
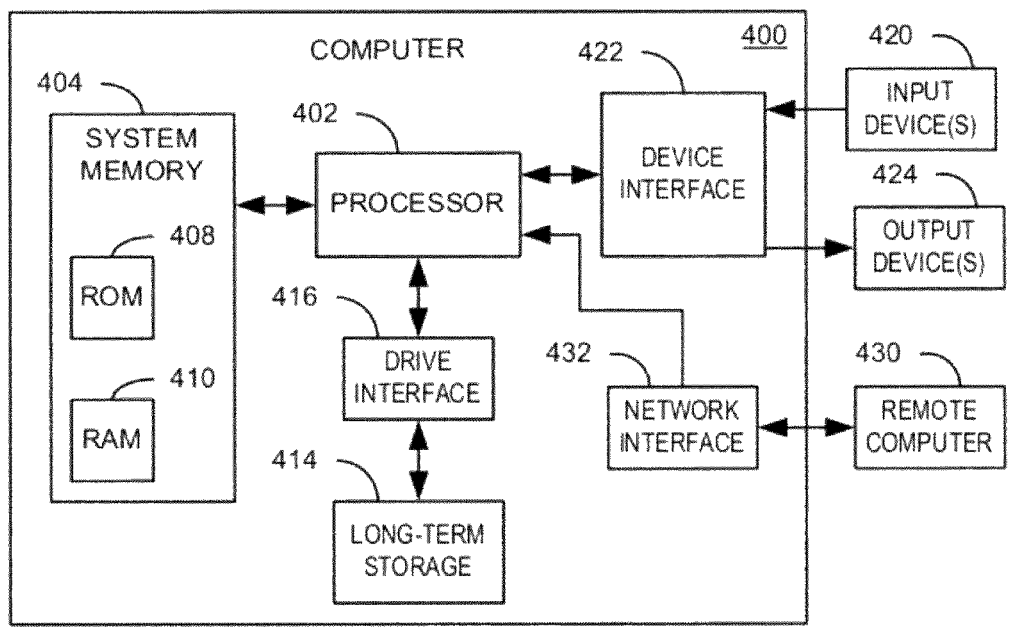
FIG. 10 illustrates a computer system that can be employed to implement systems and methods described herein, such as systems and methods based on computer executable instructions running on the computer system.

FIG. 10 illustrates a computer system 400 that can be employed to implement systems and methods described herein, such as based on computer executable instructions running on the computer system. The computer system 400 can be implemented on one or more networked general purpose computer systems, embedded computer systems, routers, switches, server devices, client devices, various intermediate devices/nodes, and/or stand alone computer systems.

The computer system 400 includes a processor 402 and a system memory 404. Dual microprocessors and other multi-processor architectures can also be utilized as the processor 402. The processor 402 and system memory 404 can be coupled by any of several types of bus structures, including a memory bus or memory controller, a peripheral bus, and a local bus using any of a variety of bus architectures. The system memory 404 includes read only memory (ROM) 408 and random access memory (RAM) 410. A basic input/output system (BIOS) can reside in the ROM 408, generally containing the basic routines that help to transfer information between elements within the computer system 400, such as a reset or power-up.

The computer system 400 can include one or more types of long-term data storage 414, including a hard disk drive, a magnetic disk drive, (e.g., to read from or write to a removable disk), and an optical disk drive, (e.g., for reading to or writing from a CD-ROM disk, a DVD, or other optical media). The long-term data storage can be connected to the processor 402 by a drive interface 416. The long-term storage components 414 provide nonvolatile storage of data, data structures, and computer-executable instructions for the computer system 400. A number of program modules may also be stored in one or more of the drives as well as in the RAM 410, including an operating system, one or more application programs, other program modules, and program data.

A user may enter commands and information into the computer system 400 through one or more input devices 420, such as a keyboard, a touchscreen, and/or a pointing device (e.g., a mouse). It will be appreciated that the one or more input devices 420 can include one or more sensor assemblies transmitting acceleration data to the computer 400 for further processing. These and other input devices are often connected to the processor 402 through a device interface 422. For example, the input devices can be connected to the system bus by one or more a parallel port, a serial port, or a USB. One or more output device(s) 424, such as a visual display device or printer, can also be connected to the processor 402 via the device interface 422.

The computer system 400 may operate in a networked environment using logical connections (e.g., a local area network (LAN) or wide area network (WAN)) to one or more remote computers 430. A given remote computer 430 may be a workstation, a computer system, a router, a peer device, or other common network node, and typically includes many or all of the elements described relative to the computer system 400. The computer system 400 can communicate with the remote computers 430 via a network interface 432, such as a wired or wireless network interface card or modem. In a networked environment, application programs and program data depicted relative to the computer system 400, or portions thereof, may be stored in memory associated with the remote computers 430.

It will be understood that the above description of the present invention is susceptible to various modifications, changes, and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for registering a sensor assembly, implemented on a mouthpiece apparatus, to a center of gravity of a head of a user, comprising:
   positioning the mouthpiece apparatus within a mouth of the user;
   determining a position and orientation of each of a plurality of sensors positioned within the mouthpiece apparatus with respect to a known landmark on an anterior portion of the mouthpiece apparatus;

measuring a position of the known landmark on the mouthpiece apparatus relative to a tragion of the user a measurement tool;

estimating the location of the tragion relative to the center of gravity from one of a known relationship and anthropometric parameters, determining the location and orientation of each sensor relative to the center of gravity according to the determined position and orientation of the sensor relative to the known landmark, the determined position of the known landmark relative to the tragion, and the position of the tragion relative to the center of gravity;

initializing the sensor assembly for the user with the determined location and orientation of the sensor assembly relative to the center of gravity.

* * * * *